United States Patent
Maloney et al.

(10) Patent No.: US 10,624,824 B2
(45) Date of Patent: Apr. 21, 2020

(54) ABRASIVE ORAL CARE COMPOSITION

(71) Applicant: Colgate-Palmolive Company, New York, NY (US)

(72) Inventors: Venda Maloney, Piscataway, NJ (US); Suman Chopra, Monroe, NJ (US); Rahul Patel, Hillsborough, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/327,670

(22) PCT Filed: Jul. 21, 2014

(86) PCT No.: PCT/US2014/047355
§ 371 (c)(1),
(2) Date: Jan. 20, 2017

(87) PCT Pub. No.: WO2016/014012
PCT Pub. Date: Jan. 28, 2016

(65) Prior Publication Data
US 2017/0252276 A1 Sep. 7, 2017

(51) Int. Cl.
| | | |
|---|---|---|
| *A61K 8/24* | (2006.01) | |
| *A61K 8/25* | (2006.01) | |
| *A61Q 11/00* | (2006.01) | |
| *A61K 8/02* | (2006.01) | |
| *A61K 8/21* | (2006.01) | |
| *A61K 8/34* | (2006.01) | |
| *A61K 8/44* | (2006.01) | |
| *A61K 8/46* | (2006.01) | |
| *A61K 8/49* | (2006.01) | |
| *A61K 8/73* | (2006.01) | |
| *A61K 8/86* | (2006.01) | |

(52) U.S. Cl.
CPC .............. *A61K 8/24* (2013.01); *A61K 8/0241* (2013.01); *A61K 8/21* (2013.01); *A61K 8/25* (2013.01); *A61K 8/345* (2013.01); *A61K 8/442* (2013.01); *A61K 8/463* (2013.01); *A61K 8/49* (2013.01); *A61K 8/73* (2013.01); *A61K 8/731* (2013.01); *A61K 8/86* (2013.01); *A61Q 11/00* (2013.01); *A61K 2800/28* (2013.01); *A61K 2800/412* (2013.01); *A61K 2800/48* (2013.01); *A61K 2800/92* (2013.01)

(58) Field of Classification Search
USPC .............................................. 424/49, 52, 53
See application file for complete search history.

(56) References Cited

U.S. PATENT DOCUMENTS

| | | | |
|---|---|---|---|
| 6,517,815 B1 | 2/2003 | Leinen et al. | |
| 8,535,730 B1 | 9/2013 | Gaffar et al. | |
| 8,741,266 B2 | 6/2014 | Boyd et al. | |
| 2004/0136929 A1* | 7/2004 | Zaidel | A61K 8/19 424/53 |
| 2005/0163729 A1 | 7/2005 | Zaidel et al. | |
| 2006/0140878 A1* | 6/2006 | Cornelius | A61K 8/25 424/49 |
| 2008/0063611 A1* | 3/2008 | Ibsen | A61K 8/11 424/52 |
| 2010/0254915 A1 | 10/2010 | Kao | |
| 2012/0237457 A1 | 9/2012 | Chen et al. | |
| 2014/0308323 A1* | 10/2014 | Midha | A61Q 11/00 424/401 |
| 2014/0377188 A1* | 12/2014 | Strand | A61K 8/0275 424/10.1 |

FOREIGN PATENT DOCUMENTS

| | | |
|---|---|---|
| CN | 1331968 A | 1/2002 |
| CN | 102772332 A | 11/2012 |
| CN | 103181858 A | 7/2013 |
| EP | 1952801 | 8/2008 |
| RU | 2155579 C2 | 9/2000 |
| WO | WO2005030141 | 4/2005 |
| WO | WO2005058263 | 6/2005 |
| WO | WO2007076396 | 7/2007 |
| WO | WO2010068442 | 6/2010 |
| WO | WO2012021415 | 2/2012 |

OTHER PUBLICATIONS

Huber Engineered Materials, "Huber Cleaning Precipitated Silicas, Quick Reference for Huber's Standard Offering of Cleaning Silica Abrasives," www.hubermaterials.com, retrieved from website Jun. 24, 2014.
International Search Report and Written Opinion of the International Searching Authority for Application No. PCT/US2014/047355, dated Mar. 17, 2015.

* cited by examiner

*Primary Examiner* — Walter E Webb

(57) ABSTRACT

The present invention provides an oral care composition comprising from 3 to 12 weight % calcium pyrophosphate and from 10 to 19 weight % precipitated silica, based on the total weight of the composition, wherein the precipitated silica has a pellicle cleaning ratio of greater than 85. The present invention further provides a method of cleaning and/or polishing and/or whitening an oral surface comprising contacting the oral surface with the oral care composition.

19 Claims, No Drawings

ABRASIVE ORAL CARE COMPOSITION

BACKGROUND

The use of abrasives in oral care compositions is well established. In addition to cleaning plaque and stains, abrasives in oral care compositions such as dentifrices can also polish the surface of enamel. The polishing of enamel has a number of cosmetic benefits including increasing the brightness and shine of teeth, imparting a smooth texture to teeth, and decreasing future discoloration through the removal of cracks and uneven surfaces which promote attachment of stains. Ideally, an abrasive or combination of abrasives can provide both cleaning and polishing of enamel.

Oral care compositions comprising calcium pyrophosphate and silica are known in the art (see for example WO2008/157197, WO2009/134657 and WO2010/068442). However, there is a need to provide oral care compositions with improved polishing action leading to high gloss or shine of the teeth without significantly increasing the abrasion of the tooth enamel.

BRIEF SUMMARY

The present invention provides an oral care composition comprising from 3 to 12 weight % calcium pyrophosphate and from 10 to 19 weight % precipitated silica, wherein the precipitated silica has a pellicle cleaning ratio of greater than 85.

Precipitated silica having a pellicle cleaning ratio (PCR) of greater than 85 when tested at 20% loading is known in the art as high cleaning silica. Typically, high cleaning silica also has a mean particle size $d_{50}$ of from 5 to 15 μm and an oil absorption of from 40 to 120 cm$^3$/100 g silica.

Preferably, the composition comprises from 3 to 12 weight % calcium pyrophosphate and from 10 to 19 weight % precipitated silica. Most preferably the composition comprises from 5 to 10 weight % calcium pyrophosphate and from 12 to 17 weight % precipitated silica.

This invention describes an oral care composition for cleaning and whitening teeth which consists of a combination of specific amounts of two abrasives. Specifically, the abrasive combination covered in this invention comprises precipitated silica having a pellicle cleaning ratio of greater than 85 and calcium pyrophosphate.

The combination of specific amounts of calcium pyrophosphate and high cleaning silica results in a surprising improvement in the polishing of enamel. Additionally, while the dentifrice formula increases the polish provided by the formula, it does not significantly increase the abrasion of the enamel. The composition of the invention provides improved polishing, leading to desirable gloss and/or shine of the teeth, whilst at the same time achieving cleaning and whitening of the teeth.

In one embodiment the oral care composition further comprises crunchy silica. The term crunchy silica is known in the art and refers to precipitated silica having a median particle size of from 300 to 500 μm. Commercially available crunchy silicas include Zeodent® 9175 "crunch" silica (Huber Engineered Materials) which has an average particle size of 450 μm, and Tixosil® G "crunchy silica" (Rhodia). The composition may comprise from 1 to 6 weight % precipitated silica having a median particle size of from 300 to 500 μm. Preferably the composition comprises 2 weight % precipitated silica having a median particle size of from 300 to 500 μm.

The oral care composition preferably further comprises a stain prevention agent. The stain prevention agent may be selected from sodium tripolyphosphate, tetrapotassium pyrophosphate, tetrasodium pyrophosphate, sodium hexametaphosphate, gantrez™ polymer or any combination thereof.

The composition may comprise from 1 to 5 weight % sodium tripolyphosphate and from 1 to 5 weight % tetrapotassium pyrophosphate, for example 2 to 3 weight % sodium tripolyphosphate and 2 to 3 weight % tetrapotassium pyrophosphate.

The composition preferably comprises a fluoride source. The fluoride source is not especially limited. Typically the fluoride source is monofluorophosphate.

The oral care composition may further comprise a surfactant, in one embodiment the surfactant is selected from sodium lauryl sulfate, cocamidopropyl betaine, and combinations thereof.

The oral care composition may further comprise a humectant. In one embodiment the humectant is selected from glycerin, sorbitol and combinations thereof.

The oral care composition may also comprise a thickening agent. The thickening agent may be selected from polyethylene glycol, a cellulose derivative, a polysaccharide gum, silica and combinations thereof. The cellulose derivative may be sodium carboxymethylcellulose. The polysaccharide gum may be xanthan gum.

The oral care composition may further comprise one or more agents selected from diluents, pH modifying agents, foam modulators, sweeteners, flavorants, pigments, preservatives, antibacterial agents, anticaries agents, anticalculus or tartar control agents, and mixtures thereof.

In a preferred embodiment the oral care composition comprises the following ingredients in weight %

| | |
|---|---|
| Sorbitol | 20-35 |
| Water | 5-40 |
| High cleaning silica | 10-19 |
| Calcium pyrophosphate | 3-12 |
| Glycerin | 5-15 |
| Silica Thickener | 2-7 |
| Polyethylene glycol | 1-5 |
| Sodium tripolyphosphate | 1-5 |
| Tetrapotassium pyrophosphate | 1-5 |
| Sodium lauryl sulfate | 1-3 |
| flavor | 1-3 |
| Cocamidopropyl betaine | 1-3 |
| Sodium CMC | 0.1-1.5 |
| Xanthan gum | 0.1-0.5 |
| Sodium saccharin | 0.1-0.5 |
| Sodium monofluorophosphate | 0.5-1.1 |

The oral care composition may be a dentifrice or a confectionary.

In a further aspect, the present invention provides a method of cleaning and/or polishing and/or whitening an oral surface comprising contacting the oral surface with an oral care composition as defined above. In a preferred embodiment the oral care composition is a dentifrice and the contacting comprises brushing of the oral care composition against the teeth.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The present invention provides an oral care composition comprising from 3 to 12 weight % calcium pyrophosphate and from 10 to 19 weight % precipitated silica, wherein the precipitated silica has a pellicle cleaning ratio of greater than 85 when tested at 20% loading.

The cleaning efficacy of the precipitated silica is expressed using the pellicle cleaning ratio (PCR). This is typically measured at 20% silica loading. The high cleaning silica preferably has a PCR value of greater than 85.

The efficacy of the precipitated silica can also be expressed with reference to its abrasive characteristic using the radioactive dentin abrasion (RDA). Ideally, RDA values for an oral composition should be below about 250 to protect tooth enamel/dentin.

Methods of performing PCR and RDA are described in e.g., U.S. Pat. Nos. 5,939,051 and 6,290,933 and "In Vitro Removal of Stain With Dentifrice", G. K. Stookey et at J. Dental Research, Vol. 61, pages 1236-9, November 1982."

Typically, the precipitated silica has a mean particle size $d_{50}$ of from 5 to 15 μm and an oil absorption of from 40 to 120 cm$^3$/100 g silica. Examples of precipitated silica having a mean particle size $d_{50}$ of from 5 to 15 μm and an oil absorption of from 40 to 120 cm$^3$/100 g silica including commercially available silicas such as Zeodent®103 and Zeodent®105 (Huber Silica Americas).

The composition may comprise from 2 to 15 weight % calcium pyrophosphate and 7-20 weight % silica, preferably from 3 to 12 weight % calcium pyrophosphate and 10 to 19 weight % silica, preferably from 5 to 10 weight % calcium pyrophosphate and 12-17 weight % silica, preferably 8 to 10 weight % calcium pyrophosphate and from 12 to 14 weight % precipitated silica; including all ranges and sub-ranges there between The composition may comprise 10 weight % calcium pyrophosphate, 11 weight % calcium pyrophosphate or 12 weight % calcium pyrophosphate. The composition may comprise 12 weight % precipitated silica, 13 weight % precipitated silica, or 14 weight % precipitated silica. The total amount of abrasive, including calcium pyrophosphate and silica, in the composition may be at most 25 weight %, preferably at most 23 weight %, preferably at most 22 weight %, based on the total weight of the composition, Mean particle size $d_{50}$ of precipitated silica particles may be measured by any means known in the art. For example, particle size may be measured using a Malvern Particle Size Analyzer, Model Mastersizer S, Malvern Instruments, Inc. (Southborough, Mass., USA), wherein a helium-neon gas laser beam is projected through a transparent cell that contains the abrasive suspended in an aqueous solution. Light rays that strike the particles are scattered through angles that are inversely proportional to the particle size. The photodetector array measures the quantity of light at several predetermined angles. Electrical signals proportional to the measured light flux values are then processed by a microcomputer system, against a scatter pattern predicted from theoretical particles as defined by the refractive indices of the sample and aqueous dispersant to determine the particle size distribution of the subject abrasive.

Oil absorption of the precipitated silica may be determined by various means known by those of skill in the art. For example, oil absorption may be determined by absorption of linseed oil or dibutyl phthalate (DBP) per 100 grams of silica. Oil absorption values can be measured using the ASTM Rub-Out Method D281. The precipitated silica utilized in the present invention typically has oil absorption of from 40 to 120 cm$^3$/100 g silica, or from 50 to 115 cm$^3$/100 g silica.

The oral care compositions of the present invention may comprise from 5 to 50 weight % water, based on the composition, preferably from 15 to 40 weight % water, preferably from 20 to 35 weight % water, and all ranges and subranges therebetween. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, amine fluorides, preferably sodium monofluorophosphate, as well as mixtures thereof. In certain embodiments, the oral care composition of the invention may also contain a source of fluoride ions or fluorine-providing ingredient in amounts sufficient to supply 25 ppm to 5,000 ppm of fluoride ions, generally at least 500 ppm, e.g., 500 to 2000 ppm, e.g., 1000-1600 ppm, e.g., 1450 ppm. Fluoride ion sources may be added to the compositions of the invention at a level of 0.01 weight % to 10 weight %, 0.03 weight % to 5 weight %, preferably 0.1 weight % to 1 weight %, most preferably 0.5 to 0.9 weight % of the composition. However, it is to be understood that the weights of fluoride salts to provide the appropriate level of fluoride ion will obviously vary based on the weight of the counter ion in the salt, and one of skill in the art may readily determine such amounts.

Compositions of the present invention may also comprise a humectant, e.g., to prevent the composition from hardening upon exposure to air. Certain humectants can also impart desirable sweetness or flavor to dentifrice compositions. The humectant, on a pure humectant basis, generally includes 15% to 70%, or 25% to 40% by weight of the oral care composition. Suitable humectants include edible polyhydric alcohols such as glycerine, sorbitol, xylitol, propylene glycol as well as other polyols and mixtures of these humectants. Mixtures of glycerine and sorbitol may be used in certain embodiments as the humectant component of the toothpaste compositions herein.

Thickening agents used in the oral care compositions of the present invention include natural and synthetic gums and colloids. Thickeners compatible with the present composition include cellulose derivatives such as carboxymethyl cellulose, hydroxyalkyl celluloses such as hydroxypropyl cellulose hydroxyethyl cellulose, polysaccharide gums such as xanthan gum, polyglycols of varying molecular weights sold under the tradename Polyox and polyethylene glycol. Inorganic thickeners which may be used in the practice of the present invention include amorphous silica compounds such as colloidal silicas compounds available under the trade designation CAB-O-SIL® manufactured by Cabot Corporation and distributed by Lenape Chemical, Bound Brook, N.J.; ZEODENT® 165 from Hither Silica Americas; and SYLODENT® 15, available from Davison Chemical Division of W. R. Grace Corporation, Baltimore, Md. 21203. Other inorganic thickeners include natural and synthetic clays, lithium magnesium silicate and magnesium aluminum silicate.

The oral care composition of the present invention may also contain flavoring agents and/or breath freshening antiplaque actives. Flavoring agents which are used in the practice of the present invention include essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Of these, the most commonly employed are the oils of peppermint and spearmint. The oral care composition may comprise a sweetener, such as sodium saccharin.

The oral care compositions of the invention may include one or more agents to increase the amount of foam that is produced when the oral cavity is brushed. Such foaming agents are known to those of skill in the art, Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of 200,000 to 7,000,000. In one embodiment the molecular weight will be 600,000 to 2,000,000 and in another embodiment 800,000 to 1,000,000. The amount of foaming agent in the oral care composition may be from 0.01 to 0.9 weight %, 0.05 to 0.5 weight %, and in another embodiment 0.1 to 0.2 weight %.

The oral care compositions of the present invention can be in the form of a dentifrice (including toothpastes, toothpowders, and prophylaxis pastes) or confectionaries (including gums, beads and chews). The compositions of the invention are not films.

The composition is safe for oral use with humans, and typically with oilier animals.

As used herein, the term "cleaning" generally refers to the removal of contaminants, dirt, impurities, and/ or extraneous matter on a target surface. For example, in the context of oral surfaces, where the surface is tooth enamel, the cleaning may remove at least some of a film or stain, such as plaque biofilm, pellicle or tartar. As used herein, "polishing" generally refers to a finishing or refining process that makes a surface smoother and/or glossier. Polishing and cleaning can also provide brightening of the surface where stain removal occurs, for example, whitening of a tooth surface. The oral surface cleaned and/ or polished and/or whitened in the present invention is typically tooth enamel.

EXAMPLES

Example 1

The general procedure for this 1600 stroke screening method is as follows:
I. Sanding Bovine Teeth
Select unstained bovine enamel specimen for sanding using a 35 grit sand paper. Sand bovine enamel specimen for 4 minutes at 100 rpms. After sanding, sort the bovine specimen and select those which have a flat surface greater than 4 mm2. 12 teeth are selected for the study.
II. Preparing Teeth
Submerge the teeth in a 1% citric acid solution in deionized water for 3 min. After 3 min rinse the teeth with deionized water and pat dry. Mount 4 teeth per tray using a thermal impression compound. Apply 6 grams of a non-aqueous toothpaste containing 35% calcium pyrophosphate to teeth and add 3 grams of deionized water in each tray. Brush the teeth for 1600 strokes using a toothbrush, 250 grams of weight, at 120 strokes/min. Rinse the toothpaste slurry from the teeth, remove the teeth from the trays, and pat dry. Brushing with the 35% calcium pyrophosphate toothpaste control brings all teeth to the same level of polish. Next repeat the 3 min soak in 1% citric acid solution, rinse the teeth with deionized water, and store in deionized water until baseline measurements.
III. Baseline Gloss Measurements
Calibrate a Novocurve glossmeter per manufacturer's instructions. Remove an enamel sample from water and pat dry. Next center the enamel surface on the glossmeter and mark the specimen to define the orientation. Take a measurement. Rotate the sample 90° and take a measurement. Rotate the sample 90° and take another measurement. Rotate the sample 90° and take another measurement. Repeat this cycle of 4 measurements then return the sample to water. Average the 8 values to get the average baseline value for gloss.
IV. Product Evaluation
Remount 4 teeth per tray using a thermal impression compound. Apply 6 grams of the test product to teeth and add 3 grams of deionized water in each tray. Brush the teeth for 1600 strokes using a toothbrush, 250 grams of weight, at 120 strokes/min. Rinse the toothpaste slurry from the teeth, remove the teeth from the trays, and submerge in water. Recalibrate the Novocurve glossmeter per manufacturer's instructions. Remove an enamel sample from water and pat dry. Next center the enamel surface on the glossmeter and mark the specimen to define the orientation. Take a measurement. Rotate the sample 90° and take a measurement. Rotate the sample 90° and take another measurement. Rotate the sample 90° and take another measurement. Repeat this cycle of 4 measurements then return the sample to water. Average the 8 values to get the average value for the gloss after treatment. Report the difference between treated and baseline gloss values as the change in gloss.
V. Cycling
To prepare the teeth for testing with the next product, repeat the acid etch, brushing with 35% calcium pyrophosphate toothpaste, and final acid etch. This process returns the teeth to a uniform baseline and allows the next test product to be evaluated on the same bovine samples.

TABLE 1

| Ingredient | (A)wt % | (B)wt % | (C)wt % | (D)wt % | (E)wt % |
| --- | --- | --- | --- | --- | --- |
| Sorbitol | 28 | 28 | 28 | 28 | 28 |
| Water | 23.25 | 23.25 | 23.25 | 23.25 | 23.25 |
| High cleaning silica | 22 | 17 | 12 | 7 | 0 |
| Calcium pyrophosphate | 0 | 5 | 10 | 15 | 22 |
| Glycerin | 7 | 7 | 7 | 7 | 7 |
| Silica Thickener | 5 | 5 | 5 | 5 | 5 |

TABLE 1-continued

| Ingredient | (A)wt % | (B)wt % | (C)wt % | (D)wt % | (E)wt % |
|---|---|---|---|---|---|
| Polyethylene glycol | 3 | 3 | 3 | 3 | 3 |
| Sodium tripolyphosphate | 3 | 3 | 3 | 3 | 3 |
| Tetrapotassium pyrophosphate | 2.44 | 2.44 | 2.44 | 2.44 | 2.44 |
| Sodium lauryl sulfate | 1.5 | 1.5 | 1.5 | 1.5 | 1.5 |
| flavor | 1.5 | 1.5 | 1.5 | 1.5 | 1.5 |
| Cocamidopropyl betaine | 1.25 | 1.25 | 1.25 | 1.25 | 1.25 |
| Sodium CMC | 0.5 | 0.5 | 0.5 | 0.5 | 0.5 |
| Xanthan gum | 0.4 | 0.4 | 0.4 | 0.4 | 0.4 |
| Sodium saccharin | 0.4 | 0.4 | 0.4 | 0.4 | 0.4 |
| Sodium monofluorophosphate | 0.76 | 0.76 | 0.76 | 0.76 | 0.76 |

TABLE 2

|  | ΔGloss |
|---|---|
| (A) 22% High cleaning silica + 0% Calpyro | 15.9 |
| (B) 17% High cleaning silica + 5% Calpyro | 19.1 |
| (C) 12% High cleaning silica + 10% Calpyro | 22.6 |
| (D) 7% High cleaning silica + 15% Calpyro | 12.4 |
| (E) 0% High cleaning silica + 22% Calpyro | 18.6 |

The results in Table 2 demonstrate that the selection of a specific amount of calpyro in combination with a specific amount of high cleaning silica provides superior polishing of enamel vs. both (A) toothpaste having only high cleaning silica and (E) toothpaste only having calpyro. These results are unexpected as it would not be foreseen that replacement of an amount of high cleaning silica with calpyro would provide a synergistic effect over the use of high cleaning silica or calpyro alone.

Example 2

Extended Experimental Method for Evaluating the Polish of Enamel
Sample Analysis
Toothpaste formulas F and G were evaluated in the Enamel Polish Potential test:

TABLE 3

| Ingredient | (F)wt % | (G)wt % |
|---|---|---|
| Sorbitol | 30 | 30 |
| Water | 22.55 | 22.55 |
| High cleaning silica | 22 | 12 |
| Calcium pyrophosphate | 0 | 10 |
| Glycerin | 7 | 7 |
| Silica Thickener | 4 | 4 |
| Polyethylene glycol | 3 | 3 |
| Sodium tripolyphosphate | 3 | 3 |
| Tetrapotassium pyrophosphate | 2.44 | 2.44 |
| Sodium lauryl sulfate | 1.5 | 1.5 |
| flavor | 1.5 | 1.5 |
| Cocamidopropyl betaine | 1.25 | 1.25 |
| Sodium CMC | 0.5 | 0.5 |
| Xanthan gum | 0.2 | 0.2 |
| Sodium saccharin | 0.3 | 0.3 |
| monofluorophosphate | 0.76 | 0.76 |

The general procedure for the widely used Enamel Polishing Potential method is as follows:

Fifty-six bovine permanent, central incisors will be cut to obtain labial enamel specimens 5×5 mm$^2$. The enamel specimens will then be embedded in an autopolymerizing methacrylate resin so that only the enamel surfaces are exposed. The blocks will be numbered and mounted on Struers polishing disks with sticky wax having their numbered sides facing each other. The bottom will be ground with a 500 grit paper, until it is completely flat. The specimens will be removed from the disks and re-mounted with the enamel specimen surface facing up. They will be ground using new 500 grit paper for 10 seconds using 5 Newtons of pressure and abundant DI water irrigation. Specimens will then be serially polished with 1200-, 2400- and 4000-grit paper for 20 seconds each. Specimens will be rinsed with deionised water for 3 minutes and air dried. Polishing/Repolishing will be manually accomplished by the use of a pumice paste (approximately 3 g LPA/2 ml distilled water) in a cloth buffer mounted in a lathe, for 5 seconds. The specimen will then be rotated 90° and polished again for 5 seconds. This will be repeated until all four directions have been polished and the specimen has been polished a total of 20 seconds.

Scoring

The specimens will be scored using the Novo-Curve Glossmeter. The specimens are scored centering the enamel surface on the Glossmeter and marking the specimen according to the lines 1, 2, 3, and 4 then rotating it 90° and scoring it again. The average of the two scores is used to calculate the Glossmeter data. The specimens will then be etched by decalcifying them in 1% HCL (v/v) tier 2 minutes to provide a dull surface to initiate the study. The gloss measurements will be repeated.

Procedure

Following the baseline (etched) scoring; the specimens will be placed on a cross-brushing machine. The brush tension will be adjusted to 150 grams, and the specimens will be brushed for 4,500 strokes with the appropriate dentifrice slurry (25 grams of dentifrice and 40 grams of deionized water) and a medium brush. The specimens will then be removed from the brushing machine, rinsed and scored once again for polish. Etching will then dull the specimens again and the entire procedures will be repeated additional times so that each product will be assayed on each tooth set. The treatment design will be a modified Latin Square design so that no treatment will follow another treatment consistently.

Calculations

The difference between the baseline score and the post-brushing score will be calculated for each specimen and represents the polish increment, Study 1: Change in gloss after 4500 strokes

TABLE 4

|  | Oral Composition | ΔGloss |
|---|---|---|
| (F) | 22% High cleaning silica[1] | 20.4 |
| (G) | 12% High cleaning silica + 10% Calpyro | 29.9 |
| (H) | Commercial toothpaste with silica which does not make a whitening or polishing claim | 17.8 |

[1]The high cleaning silica used has a PCR >85, a mean particle size $d_{50}$ of from 5 to 15 μm, and an oil absorption of from 40 to 120 cm$^3$/100 g silica.

The results in table 4 demonstrate that compositions comprising 12% High cleaning silica and 10% Calpyro (calcium pyrophosphate) provides greater polishing of enamel than a composition comprising 22% High Cleaning Silica. These results confirm the results of the screening method.

Study 2: Change in gloss after 4500 strokes.

TABLE 5

|     |                                                              | ΔGloss |
|-----|--------------------------------------------------------------|--------|
| (I) | 20% High cleaning silica + 0% Calpyro                        | 20.3   |
| (J) | 10% High cleaning silica + 10% Calpyro                       | 24.3   |
| (K) | 12% High cleaning silica + 10% Calpyro                       | 26.3   |
| (L) | Toothpaste with no high cleaning silica or calcium pyrophosphate | 7.1 |

The results in Table 5 demonstrate that a combination of 10% high cleaning silica and 10% calcium pyrophosphate also provides more polishing than a toothpaste with 20% high cleaning silica. Increasing the silica loading to 12% further improves polishing performance.

The enamel abrasivity was measured by a standard method.

Specimen Preparation

Eight (8) human enamel specimens were subjected to neutron bombardments resulting in the formation of radioactive phosphorus (32P) within the specimens under the controlled conditions outlined by the ADA. The specimens were mounted in methyl methacrylate so they lit in a V-8 cross-brushing machine. The specimens were brushed for a 5000 stroke, precondition run using slurry consisting of 10 g ADA reference material in 50 ml of a 0.5% CMC glycerin solution. The brushes used were those specified by the ADA with a brush tension of 150 g.

Procedure

Following the precondition run, the test was performed using the above parameters (150 g and 5000 strokes) in a "sandwich design." Before and after brushing with the test product (25 g product/40 ml water) each tooth set was brushed with the ADA Reference Material (10 g of $Ca_2P_2O_7$/50 ml 0.5% CMC). The procedure was repeated additional times so that each product was assayed on each tooth set. The treatment design was the modified Latin Square design so that no treatment followed another treatment consistently, Calculations One ml samples was taken, weighed (~1 g), and added to 5 ml of "Ultima Gold" scintillation cocktail. The samples were mixed well and immediately put on a liquid scintillation counter for radiation detection. Following counting, the net counts per minute (CPM) values were divided by the weight of the sample to calculate a net CPM/gram of slurry.

TABLE 6

Radioactive Enamel Abrasivity (REA). Samples A and B are not significantly different from each other.

|                                            | REA  |
|--------------------------------------------|------|
| (A) 22% High cleaning silica               | 12.7 |
| (B) 12% High cleaning silica + 10% Calpyro | 15.4 |

PCR and RDA values were measured for compositions comprising 22 weight % high cleaning silica (HCS) or 12 weight % high cleaning silica and 10% calcium pyrophosphate (Table 7).

TABLE 7

|     | 22% HCS | 12% HCS/10% Calpyro |
|-----|---------|---------------------|
| PCR | 112     | 108                 |
| RDA | 148     | 140                 |

The data in Table 7 demonstrates that the incorporation of calcium pyrophosphate does not significantly increase the abrasiveness of the composition or reduce the cleaning efficacy of the composition.

What is claimed is:

1. A single-phase oral care composition comprising;
   from 3 to 12 weight % calcium pyrophosphate, based on the total weight of the composition; and
   from 10 to 19 weight % of precipitated silica, based on the total weight of the composition,
   wherein the precipitated silica has a mean particle size (d50) of from 5 to 15 μm and an oil absorption of from 40 to 120 cm$^3$/100g, and wherein the precipitated silica has a pellicle cleaning ratio of greater than 85 when tested at 20% loading; and
   wherein the composition comprises no more than 22 weight % of abrasives, including calcium pyrophosphate and precipitated silica, based on the total weight of the composition.

2. The oral care composition according to claim 1, wherein the composition comprises from 5 to 10 weight % or from 8 to 10 weight % calcium pyrophosphate, based on the total weight of the composition; and from 12 to 17 weight % or from 12 to 14 weight % precipitated silica, based on the total weight of the composition.

3. The oral care composition according to claim 1, wherein the composition comprises 10 weight % calcium pyrophosphate and 12 weight % precipitated silica; or wherein the composition comprises 12 weight % calcium pyrophosphate and 10 weight % precipitated silica.

4. The oral care composition according to claim 1, wherein the composition further comprises a stain prevention agent selected from sodium tripolyphosphate, tetrapotassium pyrophosphate, tetrasodium pyrophosphate, sodium hexametaphosphate, or any combination thereof.

5. The oral care composition according to claim 4, wherein the stain prevention agent comprises from 1 to 5 weight % sodium tripolyphosphate, based on the total weight of the composition; and from 1 to 5 weight % tetrapotassium pyrophosphate, based on the total weight of the composition.

6. The oral care composition according to claim 1, wherein the composition further comprises a fluoride source.

7. The oral care composition according to claim 6, wherein the fluoride source is at least one selected from stannous fluoride, sodium fluoride, potassium fluoride, sodium monofluorophosphate, sodium fluorosilicate, ammonium fluorosilicate, amine fluoride, and ammonium fluoride.

8. The oral care composition according to claim 6, wherein the fluoride source is sodium monofluorophosphate.

9. The oral care composition according to claim 6, wherein the fluoride source is sodium fluoride.

10. The oral care composition of claim 1, further comprising a surfactant selected from sodium lauryl sulfate, cocamidopropyl betaine, and combinations thereof.

11. The oral care composition of claim 1 further comprising a humectant selected from glycerin, sorbitol and combinations thereof.

12. The oral care composition according to claim 1 further comprising a thickening agent.

13. The oral care composition of claim 12, wherein the thickening agent is selected from polyethylene glycol, a cellulose derivative, a polysaccharide gum, silica and combinations thereof.

14. The oral care composition of claim 13, wherein the cellulose derivative is sodium carboxymethylcellulose.

15. The oral care composition of claim 13, wherein the polysaccharide gum is xathan gum.

16. An oral care composition according to claim 1, wherein the composition further comprises one or more agents selected from diluents, pH modifying agents, foam modulators, sweeteners, flavorants, pigments, preservatives, antibacterial agents, anticaries agents, anticalculus or tartar control agents, and mixtures thereof.

17. An oral care composition according to claim 1 which is a dentifrice or a confectionary.

18. A method of cleaning and/or polishing and/or whitening an oral surface comprising contacting the oral surface with an oral care composition as defined in claim 1.

19. A method according to claim 18, wherein the oral care composition is a dentifrice and the contacting comprises brushing of the oral care composition against the teeth.

\* \* \* \* \*